(12) United States Patent
Schiller

(10) Patent No.: US 6,296,611 B1
(45) Date of Patent: Oct. 2, 2001

(54) MEASURING ARRANGEMENT

(76) Inventor: Alfred Schiller, Steinenstückiweg, 8914 Aeugst a.A. (CH)

( * ) Notice: Subject to any disclaimer, the term of this patent is extended or adjusted under 35 U.S.C. 154(b) by 0 days.

(21) Appl. No.: 09/252,689

(22) Filed: Feb. 22, 1999

(30) Foreign Application Priority Data

Feb. 26, 1998 (EP) ................................................. 98810156

(51) Int. Cl.⁷ ...................................................... A61B 5/00
(52) U.S. Cl. ........................................................... 600/454
(58) Field of Search .................................. 600/453, 455, 600/454, 457, 456

(56) References Cited

U.S. PATENT DOCUMENTS

| | | | |
|---|---|---|---|
| 4,476,874 | * 10/1984 | Taenzer et al. | 600/454 |
| 4,582,066 | 4/1986 | Barnes et al. | |
| 5,348,015 | * 9/1994 | Moehring et al. | 600/453 |
| 5,409,010 | * 4/1995 | Beach et al. | 600/455 |

FOREIGN PATENT DOCUMENTS

| | | |
|---|---|---|
| 0 139 285 A2 | 10/1984 | (EP) . |
| 0 421 465 A2 | 10/1990 | (EP) . |
| 91 16000 A | 10/1991 | (WO) . |

* cited by examiner

*Primary Examiner*—Marvin M. Lateef
*Assistant Examiner*—Maolin Patel
(74) *Attorney, Agent, or Firm*—Shoemaker and Mattare, Ltd.

(57) ABSTRACT

An arrangement for measuring the blood flow from a multitude of individual flow measuring units (11, 11') arranged next to one another. The multitude of individual flow measuring units arranged next to one another permit a quick placing on of the measuring arrangement. Independently of the exact location on the human body on which the measuring arrangement is placed, always one artery, in particular the carotid artery lies neighbouring at least one of the flow measuring units.

8 Claims, 3 Drawing Sheets

MEASURING ARRANGEMENT

The invention relates to a measuring arrangement with the features of patent claim 1.

It is known with a cardiac arrest or heart malfunctioning to apply electroshocks or cardiac massage in order to stimulate cardiac activity again. Defibrillators (for producing electroshocks) or cardiac massage apparatus are often applied with first aid treatment.

It is important to know at which point in time and whether a defibrillation or a cardiac massage must be carried out. With the onset of a heart beat further heart beats should be supported by way of directed current shocks or massage. A defibrillation should only be carried out when with the patient no pulse can be ascertained. Usually with this the (carotid) pulse of the patient is manually felt. With this above all with a weak pulse a superposition of the pulse of the patient with the pulse of the helper may occur.

The blood circulation of the head must be recreated within three minutes after a cardiac arrest in order to prevent irreparable brain damage. It is therefore necessary to be able to determine the pulse as quickly as possible.

With all applications of defibrillations the mechanical activity of the heart is acquired. Since often in the extremities of the patient a hypoxaemia prevails, the carotid pulse at the carotid artery is measured.

Above all with first aid measures it is important that with the determination of the pulse no time is lost. Not only with the reanimation by way of cardiac massage or defibrillation, but also in other situations the rapid and reliable determination of the pulse is of a significant importance.

It is the object of the present invention to avoid the disadvantages of that which is known and to provide an arrangement for determining the pulse which avoids a troublesome search of the carotid artery and which permits a quick determination of the pulse.

According to the invention this object is achieved with an arrangement with the features of the independent patent claim 1.

First of all the invention relates to a flow measuring arrangement which is particularly suitable for determining the pulse. Of course the subsequently described inventive idea may likewise be advantageously applied to other measuring methods with which it is a case of a quick measurement.

According to the invention the arrangement for measuring the pulse involves a flow measurement. By measuring the blood flow, in particular into the head, the pulse of a patient may be determined.

Blood flow in this context is to be understood at the volume of blood which is pumped from the heart into the head part per unit of time. The blood flow may be measured most simply at the carotid artery.

For measuring the blood flow principally any flow measuring arrangements may be used. Particularly advantageous is a measuring cell based on the Doppler effect. Doppler measurements for determining the speed of the blood in blood vessels are already known for diagnostic purposes.

Since with a cardiac arrest the reanimation must be started as quickly as possible no time may be lost in order to localise the carotid artery for placing on the arrangement for measuring the blood flow. According to the present invention the arrangement for the non-invasive measurement of the blood flow consists of a multitude of measuring units arranged next to one another. The signal outputs of the individual flow measuring units are coupled to a signal processing arrangement. The relative position, the number and/or size of the flow measuring units is at the same time selected in such a manner that even with a measuring arrangement placed on the carotid artery roughly at right angles, in each placed on position at least one fluid measuring unit is adequately close to the carotid artery that a measurable measurement signal is produced. Roughly at right angles in this case means the measuring units lying next to one another are applied transversely onto the carotid artery. Thanks to this embodiment form the measuring arrangement according to the invention may be layed onto the neck of the patient without an exact placing on being necessary. Independently of how the arrangement is applied onto the neck of the patient always one flow measuring unit is correctly positioned on the carotid artery.

It is of course to be understood that such a measuring arrangement may be particularly advantageously used with a reanimation by way of defibrillation or cardiac massage. It is however also completely conceivable to use the measuring arrangement in other fields of application where a quick determination of the blood flow is required.

Advantageously the measuring arrangement comprises about 3 to 10 measuring units arranged next to one another. Each measuring unit has a surface with approx. 4 mm diameter to 8 mm diameter. As measuring units preferably piezoelectric measuring cells based on the measurement of the Doppler effect are used. It is however also conceivable to arrange other known measuring units in the way and manner according to the invention.

Advantageously a row of transducer elements lying next to one another are used. Transducers functioning with the pulsed wave as well as with the continuous wave method may be applied.

Alternatively it is conceivable to provide two rows of transducers arranged displaced to one another. As a result the probability that in each case a transducer comes to lie on the carotid artery may be increased to almost 100%.

In the following the invention is described in more detail in embodiment examples and by way of the drawings.

There are shown:

Figure 1:
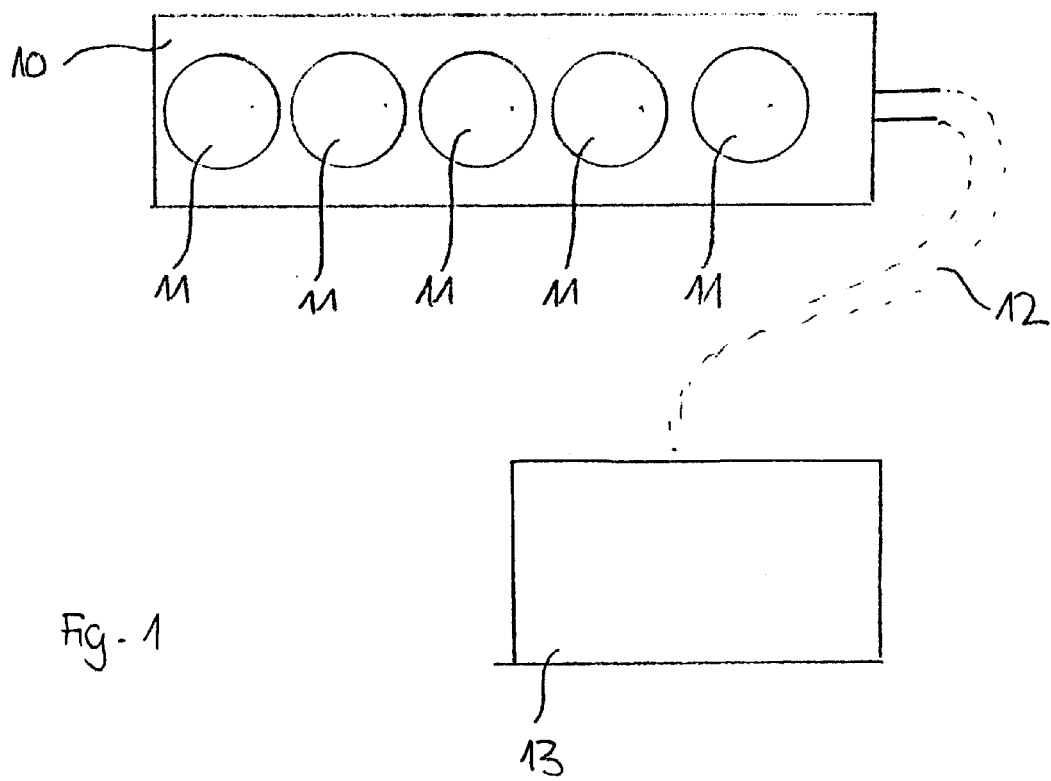
FIG. 1 is a schematic representation of a measuring arrangement.

FIG. 1 shows schematically a measuring arrangement 10 according to the invention, for the non-invasive measurement of the blood flow. The measuring arrangement 10 consists of five flow measuring units 11 arranged next to one another. The outputs 12 of the flow measuring units 11 are coupled to a signal processing arrangement 13. The flow measuring units 11 have a diameter of 4 to 5 mm. Measuring units based on the principle of the Doppler effect measurement are used in the pulsed or continuous wave method. According to the purpose of application the frequency range of the transducer varies. For measuring the carotid pulse a frequency of 8 MHz is applied. For determining the pulse at deeper lying arteries, frequencies of 4 or 2 MHz may be applied.

Figure 6:
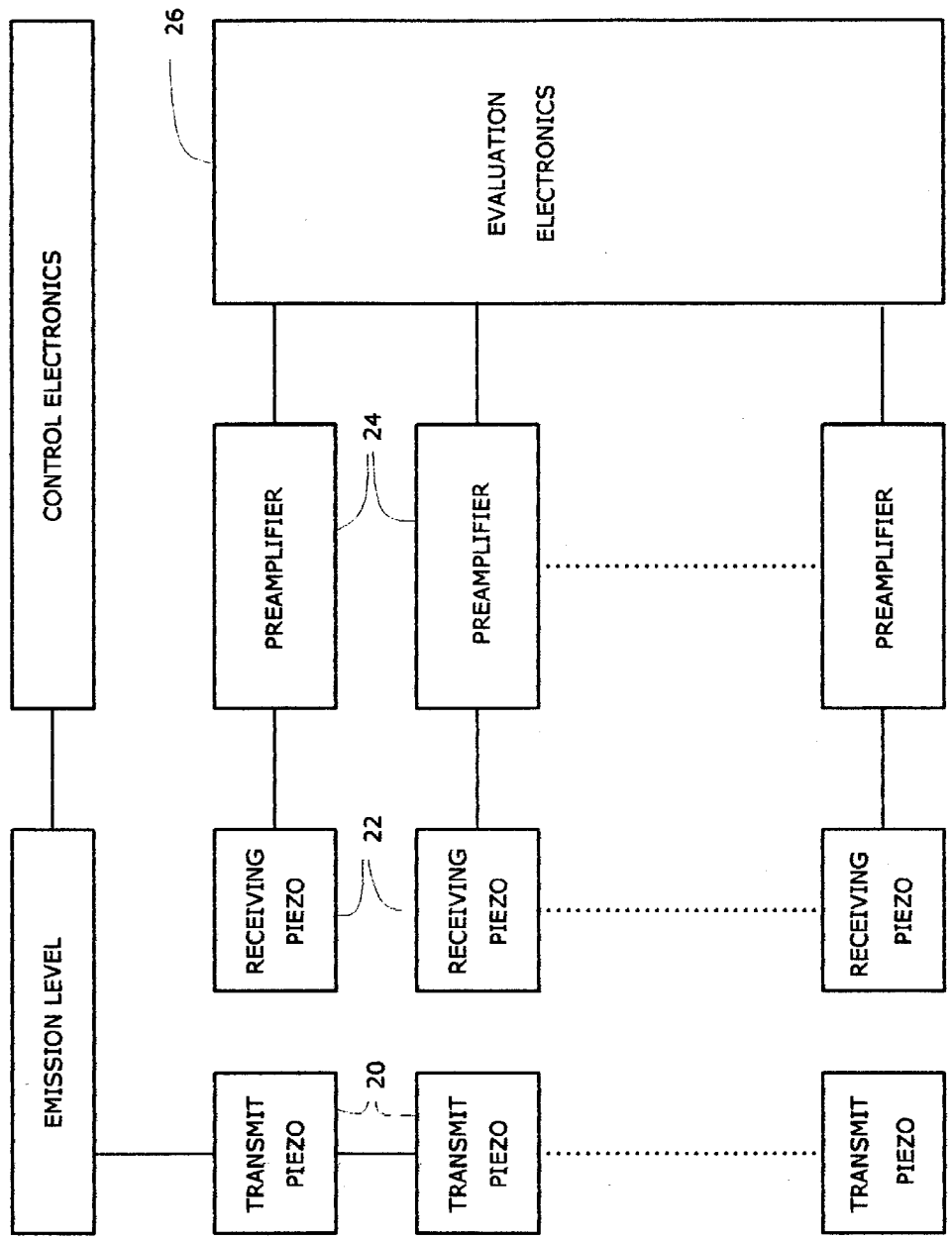
FIG. 6 is a schematic diagram of the electrical components of the invention.

Typically each flow measuring unit 11 comprises (FIG. 6) a transmitter 20 and a receiver 22 (piezoelectric elements). The transmitter produces continuous oscillations. The receiver acquires the sound waves reflected by the blood platelets and computes (in the known manner) the speed of the blood on account of the frequency shift (Doppler effect). This means that firstly the speed of the blood is measured. The rate of the blood flow is proportional to the speed. The signal of the receiver 22 is amplified via a preamplifier 24 and is led into the signal processing arrangement 13. Typically the output of each receiver is given to a preamplifier. The outputs of the preamplifier are coupled to a commercially available chip 26 with several inputs (e.g. H8 from Hitachi). The chip evaluates the strongest signal and produces an output signal corresponding to the strength of the strongest signal.

Figure 5:
FIG. 5 is a schematic representation of the measuring arrangement used on a patient.

If the measuring arrangement 10 according to the invention is layed onto for example the neck of a patient (see FIG. 5) always one of the flow measuring units 11 lies on or neighbouring the carotid artery. This flow measuring unit 11a produces a signal which represents the value of the blood flow. The remaining flow measuring units which do not lie directly neighbouring the carotid artery produce a weaker or no signal.

Of course it is however also conceivable with a signal processing arrangement 13 to take into account the readings of all flow measuring units and to compute an integrated signal. This may above all be advantageous with arrangements with which the dimensions of the flow measuring units 11 are selected such that that more than one flow measuring unit 11 simultaneously lies neighbouring the carotid artery.

Figure 2:
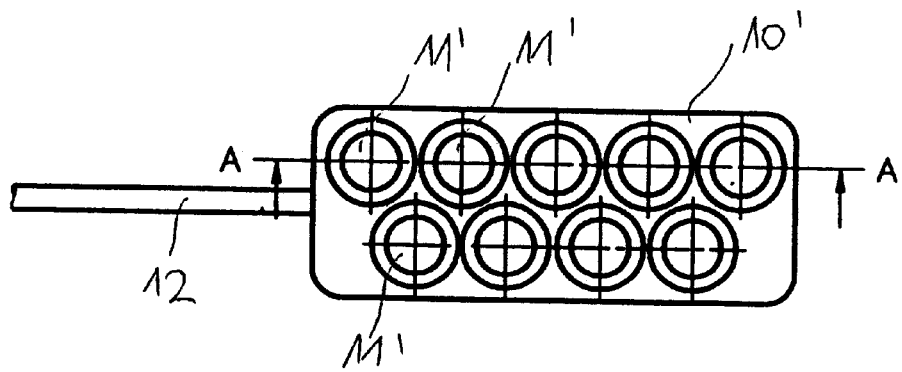
FIG. 2 is an alternative embodiment example of a measuring arrangement.
Figure 3:
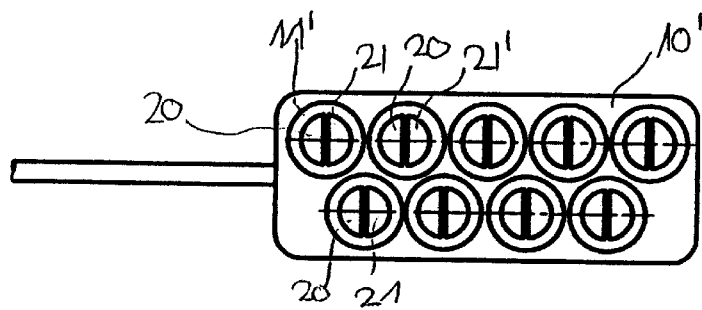
FIG. 3 is further embodiment example of a measuring arrangement.

In FIGS. 2 and 3 there is shown an alternative embodiment example of a measuring arrangement 10'. The individual flow measuring units 11' are arranged in two rows displaced to one another. With this the resolution may be increased or the probability of a flow measuring unit in each case lying exactly on the carotid artery is increased. According to the embodiment example in FIG. 2 the flow measuring units 11 consist of pulsed transducer elements which simultaneously transmit and receive.

In FIG. 3 the flow measuring units 11 consist each of a transmitter 20 and a receiver 21. The transmitter 20 and receiver 21 are transducer elements operated in the continuous wave method.

The individual flow measuring units 11, 11' may be cast in silicone rubber or also rigidly connected to one another.

Figure 4:
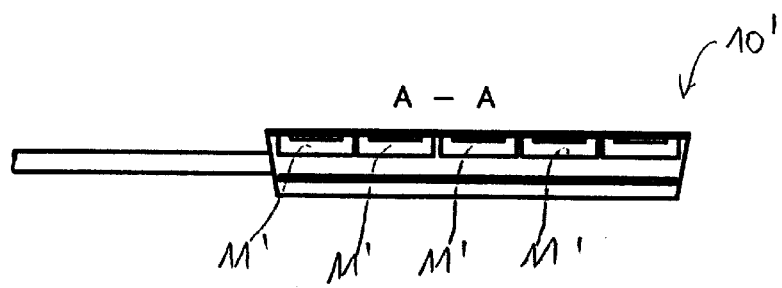
FIG. 4 is the measuring arrangement according to FIG. 2 in the cross section along a line A—A.

FIG. 4 shows the measuring arrangement 10' according to FIG. 2 in cross section. Five flow measuring units 11' are arranged next to one another and lie essentially in a plane.

Whilst previously the application of the measuring arrangement according to the invention was above all explained in the context of first aid measures, a measuring arrangement with a multitude of measuring units arranged next to one another can of course also be used in other application purposes, where it is a case of a quick determination of a measurement signal. The basic concept of the invention lies in the fact that a multitude of individual measuring cells are used of which independently of the way and manner of the placing on of the measuring arrangement, always one produces a signal.

What is claimed is:

1. A measuring arrangement for non-invasive measurement of blood flow in an artery, said arrangement comprising a plurality of flow measuring units arranged in an array, each of said flow measuring unit producing an output signal, all of said output signals being coupled to a signal processor, said flow measuring units being arranged within the array proximate to one another so that when the arrangement is placed over an artery, at least one flow measuring unit lies sufficiently close to the artery that an output signal detectable by the signal processor is produced.

2. An arrangement according to claim 1, wherein the arrangement (10) comprises 4 to 10 flow measuring units (11).

3. A measuring arrangement according to claim 1, wherein each flow measuring unit has a diameter of 0.4 to 1 cm.

4. A measuring arrangement according to claim 1 wherein the flow measuring units (11, 11') are Doppler effect measuring units functioning in the continuous wave method.

5. A measuring arrangement according to claim 1 wherein the flow measuring units (11, 11') are Doppler effect measuring units functioning in the pulsed method.

6. An arrangement according to one of claim 1 wherein the flow measuring units are arranged next to one another in a row.

7. An arrangement according to claim 1, wherein the flow measuring units are arranged displaced to one another in two rows.

8. A method for the non-invasive measurement of blood flow in an artery, said method comprising steps of applying an array of measuring units to a body in the region of the artery, obtaining an output signal from each of said measuring units, and evaluating at least the strongest of said output signals.

* * * * *